(12) United States Patent
Wettling et al.

(10) Patent No.: US 6,437,021 B1
(45) Date of Patent: Aug. 20, 2002

(54) BIOCIDE MATERIAL AND METHOD OF PREPARATION OF SAID MATERIAL

(75) Inventors: Danielle M. Wettling, Chatenoy le Royal (FR); Karen Leeming, Bushey (GB); Sylvie Lebrat, Chalon sur Saone (FR); Christopher P. Moore, Harrow (GB); Thierry Janet, Saint Germain du Plain (FR)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 09/856,967

(22) PCT Filed: Nov. 18, 1999

(86) PCT No.: PCT/EP99/08863

§ 371 (c)(1),
(2), (4) Date: May 25, 2001

(87) PCT Pub. No.: WO00/30443

PCT Pub. Date: Jun. 2, 2000

(30) Foreign Application Priority Data

Nov. 25, 1998 (FR) .............................. 98 15009

(51) Int. Cl.[7] ................................ C08K 5/34

(52) U.S. Cl. ................ 523/122; 524/83; 424/78.08; 424/405; 424/409

(58) Field of Search .................... 523/122; 524/83; 424/405, 409, 78.08

(56) References Cited

U.S. PATENT DOCUMENTS 6,270,786 B1 * 8/2001 Leeming et al. ............ 424/409

FOREIGN PATENT DOCUMENTS

| EP | 0 733 303 A | 9/1996 |
|----|-------------|--------|
| EP | 0 733 304 A | 9/1996 |
| GB | 1 433 303 A | 4/1976 |

* cited by examiner

Primary Examiner—Kriellion A. Sanders
(74) Attorney, Agent, or Firm—Chris P. Konkol

(57) ABSTRACT

This invention relates to a biocide material to inhibit the growth of micro-organisms in an aqueous solution, a device comprising such a material, and a method of preparation of such a polymeric material.

The biocide material of the invention comprises a water-insoluble polymeric support on which a biocide is immobilized, the water content of the material being between 30 and 60% by weight of the material.

13 Claims, No Drawings

BIOCIDE MATERIAL AND METHOD OF PREPARATION OF SAID MATERIAL

This invention relates to a biocide polymer material designed to inhibit the growth of micro-organisms in an aqueous solution, a device comprising said material, and a method to prepare said material-This invention also relates to a method to inhibit the growth of micro-organisms using said material.

When systems involving water, aqueous dispersions or aqueous solutions are used, growth of micro-organisms occurs with time, adversely affecting such systems.

This problem is particularly acute in the domain of photography. Conventionally, a photographic process includes several processing baths, which are aqueous solutions of photographically active substances. The photographic products are processed by successive immersion in these different solutions. During the processing, fragments of gelatin from the photographic material being processed accumulate in the processing baths, favoring the growth of micro-organisms.

Such growth, if it is not controlled, causes the formation of biofilms in the processing baths. These biofilms clog flows and significantly reduce the activity of the processing baths, thereby impairing the quality of the photographic images obtained.

To avoid such problems arising from the growth of micro-organisms, biocides are conventionally added to processing baths. These biocides are generally used in excess of the quantity necessary to inhibit the growth of micro-organisms. These biocides can be costly and toxic. In particular, the disposal of such compounds in the drains causes problems in waste water treatment plants that use the action of micro-organisms to treat sewage.

The quantity of biocide used can be reduced by various means. For example, patent application GB 2 223 662 describes an organic biocide chemically attached to a polymer by a bond that is cleaved by hydrolysis. The polymer is progressively hydrolysed, releasing the biocide in a controlled manner. However, this release of biocide does not depend on the presence of micro-organisms in the medium.

Patent application EP 733303 describes a biocide material comprising an organic biocide immobilized on a polymer support that is insoluble in water. The biocide is attached to the polymer by hydrolytically stable bonds.

Patent application EP 733304 describes a biocide material comprising a biocide of which the Log P value is at least 1.5, in which the biocide is immobilized on a support the surface of which is hydrophobic, by a mechanism of hydrophobic exclusion, P being the partition coefficent between n-octanol and water.

In such materials, the biocide is used "as required" whenever micro-organisms are present in the solution to be treated.

It is desirable to have a biocide material comprising a biocide consumed "as required" solely in the presence of micro-organisms, having a high inhibiting efficiency.

The invention relates to a biocide material comprising a water insoluble polymer support having immobilized thereon a biocide wherein the biocide material contains a water content from 30 to 60% based on the material weight.

The invention also relates to a method of preparation of said material, which comprises the following steps:

(i) Solubilizing a biocide in an organic solvent,
(ii) Contacting the biocide solution with a water-saturated water-insoluble polymer support in conditions such that the biocide is immobilized on the polymer support,
(iii) Removing the organic solvent,
(iv) Partially removing the water contained in the polymer support having immobilized thereon biocide to obtain a water content between 30 and 60% by weight.

Lastly, the invention relates to a method to inhibit the growth of micro-organisms in an aqueous solution, by contacting the aqueous solution with the biocide material of the invention, and a device to implement this method.

Biocides are compounds able to kill micro-organisms or inhibit the multiplication of micro-organisms such as bacteria, yeast, algae, molds, and lichens. Such compounds are known to the art. Examples of biocides are described in "Microbiocides for the protection of materials", by W. Paulus, published by Chapman Hall, 1993.

Such biocides include sulfur- or nitrogen-containing heterocycles, compounds comprising active halogen groups, and quaternary ammonium salts.

In one embodiment of this invention, the biocides are isothiazolinones.

The isothiazolinones useful in this invention can be represented by the formula:

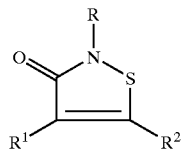

wherein R represents a hydrogen atom, an alkyl group, an aryl group, an alkylaryl group, or an arylalkyl group, and $R^1$ and $R^2$ each independently represent a hydrogen atom, a halogen, an alkyl group, or $R^1$ and $R^2$ jointly represent the atoms necessary to form a condensed carbocycle, preferably comprising 5 or 6 members, for example a benzene ring.

Preferred biocides can be represented by the following formulae (I) or (II)

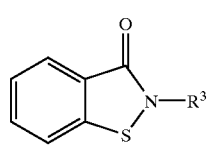

(I)

wherein $R^3$ is an alkyl group comprising 4 to 20 carbon atoms or an aryl group comprising 6 to 20 carbon atoms,

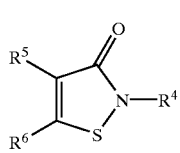

(II)

wherein $R^5$ is and $R^6$ are selected from a hydrogen atom or a halogen atom, and $R^4$ is an alkyl group comprising 1 to 20 carbon atoms.

Such biocides include for example Proxel® and Promexal® marketed by Zeneca, and Kathon® marketed by Rohm and Haas.

The polymer support useful in the scope of the invention is any support, insoluble in water and on which a biocide can be immobilized.

Useful polymers are for example the polymers obtained by condensation, such as polyesters, polyamides, polyurethanes, polyethers, epoxy resins, amino resins, phenol-aldehyde resins and acrylic polymers, and polymers derived from ethylenically unsaturated monomers such as polyolefins; polystyrene, polyvinyl chloride, polyvinyl acetate, etc.

The polymer support may have any of various shapes, for example sheets, beads, fibers, etc. It may be porous or non-porous.

The support is usually inert towards the solutions to be treated. However, it can also be a resin that allows the composition of the solution to be treated to be modified in a controlled way, for example an ion exchange resin.

In the method of preparation of the invention, the biocide is dissolved in an organic solvent. For this purpose one or more biocides is dissolved in one organic solvent or in a mixture of organic solvents. The organic solvent or solvents usefil in the scope of the invention are for example heptane, hexane, dichloromethane, ethyl acetate, tetrahydrofiran or toluene.

Depending on the nature of the biocide, support or solution to be treated, the solution concentration can vary largely. However, the concentration of biocide in the organic solvent or solvents is usually at least 0.2 mol/l, preferably between 0.2 mol/l and 1 mol/l, and preferably between 0.25 mol/l and 0.50 mol/l.

The biocide material is formed by contact between the biocide solution and the water-saturated polymer support in conditions such that the biocide is immobilized on the polymer support.

There are numerous ways to immobilize the biocide on the polymer support.

According to the selected immobilization method, those skilled in the art are able to define the chemical steps required.

In a preferred embodiment, the biocide is immobilized by a mechanism of hydrophobic exclusion. In this case, the biocide must have a log P value of at least 1.5, P being the partition coefficient between n-octanol and water defined by $$P=[\text{biocide}]_{octanol}/[\text{biocide}]_{water}$$

The value of Log P is well known in the literature concerning biocides. The values given hereafter are calculated by the method of V. Vishwanadan, A. Ghose, G. Revankar and R. Robins in "J. Chem. Inf Comput. Sci.", 1989, 29, 163.

In this type of mechanism of immobilization, when the biocide has a value of Log P less than 1.5, it can detach itself from the polymer support and contaminate the aqueous medium even when no micro-organisms are present. In this case, the advantage of the invention is not obtained, because the biocide is not released "as required".

Supports particularly suitable to immobilize the biocide by hydrophobic exclusion are supports with hydrophobic surfaces, for example cross-linked polystyrene beads, preferably porous. Such beads are marketed under the names Amberlite XAD-4® and Amberlite XAD-2®. In another embodiment, the support is a polyacrylic resin, for example Amberlite XAD-7®.

When the immobilization of the biocide on the support is carried out by hydrophobic exclusion, the biocide material can be obtained merely by contacting the biocide solution with the water-saturated polymer support for a sufficient time to immobilize the biocide on the support. The contacting can be speeded up with stirring. The duration of contact between the polymer support and the biocide can range widely according to the support and the biocide selected. The optimum contact duration can be easily determined by those skilled in the art according to the substances present.

In an embodiment of the invention, the water and the solvent are eliminated by distillation.

Preferably, the water content of the biocide material is between 35 and 40% by weight of the material.

According to the shape of the polymer support, a biocide material in the form of sheets, particles, fibers, etc., can be obtained.

The biocide material of the invention, when it is contacted with an aqueous solution in which micro-organisms may grow, inhibits the growth of any such micro-organisms.

The contact between the biocide material and the solution to be treated can be effected in any of various known ways. For example, the biocide material of the invention or the device that makes use of such a material can be placed in a circuit in which the solutions to be treated flow, in order to optimize the contact between the micro-organisms and the biocide. The device can, for example, use the biocide material in the form of particles placed in a container through which the aqueous solution to be treated flows. The solution to be treated can also flow over strips of the biocide material. When the biocide material is porous, the solution to be treated can be allowed to percolate through the biocide material.

The material of the invention is especially well-suited to the treatment of photographic solutions for processing and washing photographic elements.

The following examples illustrate the invention in detail.

EXAMPLE 1

COMPARATIVE

In this example, 13 g of biocide Kathon 287T® marketed by Rohm and Haas (4,5-dichloro-n-octyl-4-isothiazolin-3-one, Log P value=3.66) was dissolved in 170 ml of heptane (0.27 mol/l ). 100 g of beads of Amberlite XAD-7® polyacrylic resin were washed twice with 2×100 ml of water to saturate the beads with water. After washing, the water content of the beads was about 65% by weight.

The solution of biocide and the water-saturated resin beads were then placed in contact in a stirred reactor maintained at 40° C. for 1 5 minutes in order to immobilize the biocide on the polymer support.

After 15 min. all the solvent and most of the water were removed by distillation under reduced pressure.

In this way a biocide material containing a minimal quantity of water (7% by weight) was obtained.

These beads were placed in a glass column 10 cm by 1 cm and retained by a nylon filter 300 microns in thickness. The beads were then placed in contact with a stationary culture of *Pseudomonas aeriginosa* using the following operating procedure.

45 mnl of sterile distilled water was placed in a flask. The column was then connected to the flask to form a circulation loop, one of the tubes being equipped with a peristaltic pump, the flow rate of which was set at 12.5 ml/min.

The flask, maintained at 30° C., was inoculated so as to contain about $10^9$ bacteria per ml.

The number of growing colonies on inoculation and then after 1, 3, 5, 7 and 24 hours operation was counted using a colony counter. These were plotted to give the number of colony forming units (cfu) versus time.

From these values the speed of kill of the bacteria was calculated using the formula:

Log(cfu/ml)/h

This procedure was repeated three times, and an average value of the speed of kill of the bacteria was then calculated.

The same experiment was carried out using a control column containing beads of Amberlite XAD-7® but no immobilized biocide.

The average speed of kill of the bacteria is reported in table 1 below.

EXAMPLE 2

INVENTION

The operating procedure of example 1 was repeated but the water in the biocide material was removed so as to obtain a water content of about 37%.

The average speed of kill of the bacteria is reported in table 1 below.

EXAMPLE 3

INVENTION

The operating procedure of example 1 was repeated but the water in the biocide material was removed so as to obtain a water content of about 50%.

The average speed of kill of the bacteria is reported in table 1 below.

TABLE 1

|  | Speed of kill of bacteria Log (cfu)/ml)/h | |
| --- | --- | --- |
|  | Control | with immobilized biocide |
| Example 1 | −0.07 | −0.5 |
| Example 2 | −0.05 | −2.4 |
| Example 3 | −0.07 | −2 |

These results show the influence of the water content of the biocide material on the efficiency of the material. It is clearly demonstrated with these examples that having a biocide material having a specific water content provides an improvement of the speed of kill of bacteria.

The invention has been described in detail with particular reference to certain preferred embodiments thereof, but it will be understood that variations and modifications can be effected within the spirit and scope of the invention.

What is claimed is :

1. A biocide material comprising a water insoluble polymer support having immobilized thereon a biocide wherein the biocide material contains a water content from 30 to 60% based on the material weight.

2. The biocide material of claim 1 wherein the water content is from 35% to 40%.

3. The biocide material of claim 1 wherein the biocide is an isothiazolinone.

4. The biocide material of claim 1 wherein the polymer support is in the form of beads.

5. The biocide material of claim 1 wherein the polymer support has a hydrophobic surface, the biocide has a log P value of at least 1.5, and the biocide is immobilized on the support by hydrophobic exclusion.

6. A method of preparation of a biocide material as defined in claim 1, that comprises the following steps:

(i) Solubilizing a biocide in an organic solvent, (ii) Contacting the biocide solution with a water-saturated water-insoluble polymer support in conditions such that the biocide is immobilized on the polymer support, (iii) Removing the organic solvent, (iv) Partially removing the water contained in the polymer support having immobilized thereon biocide to obtain a water content between 30 and 60% by weight.

7. The method of claim 6 wherein the step (iv) is conducted until the water contained in the biocide material is from 35 to 40%.

8. The method of claim 6 wherein the organic solvent is selected from heptane, hexane, toluene, ethyl acetate.

9. The method of claim 6 wherein the organic solvent and water are removed by distillation.

10. The method of claim 6 wherein the biocide is an isothiazolinone.

11. The method of claim 10 wherein the concentration of biocide in the organic solvent is at least 0.2 mol/l.

12. A method to inhibit the growth of micro-organisms in an aqueous solution that comprises contacting the aqueous solution with the biocide material as defined in claim 1.

13. A device to inhibit the growth of micro-organisms that comprises the biocide material as defined in claim 1.

* * * * *